(12) United States Patent (10) Patent No.: US 7,805,981 B2
Kadlecek et al. (45) Date of Patent: Oct. 5, 2010

(54) GASEOUS NUCLEAR SYMMETRIC STATE AND QUANTIFICATION THEREOF

(75) Inventors: Steve Kadlecek, Philadelphia, PA (US); Rahim Rizi, Ambler, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 404 days.

(21) Appl. No.: 12/068,963

(22) Filed: Feb. 13, 2008

(65) Prior Publication Data

US 2008/0236250 A1 Oct. 2, 2008

Related U.S. Application Data

(60) Provisional application No. 60/901,362, filed on Feb. 13, 2007.

(51) Int. Cl.
*G01N 29/024* (2006.01)
*G01N 26/036* (2006.01)
(52) U.S. Cl. .................................... 73/24.06
(58) Field of Classification Search ...... 73/24.01–24.06
See application file for complete search history.

(56) References Cited

U.S. PATENT DOCUMENTS 4,403,500 A * 9/1983 Le Baud .................... 73/19.05

FOREIGN PATENT DOCUMENTS

JP 59119248 A * 7/1984

OTHER PUBLICATIONS

Vandat et al., "Method for Continuous Measurement of Nuclear Para State Enrichment in Hydrogen Gas with Applications to Hyperpolarized Heteronuclear Contrast Agents," Nov. 26, 2006, RNSA LL-PH4181-B07, two pages.*

* cited by examiner

*Primary Examiner*—John Fitzgerald
(74) *Attorney, Agent, or Firm*—Pearl Cohen Zedek Latzer, LLP; Mark S. Cohen

(57) ABSTRACT

This invention relates to methods and apparatus of quantifying the portion of a gas in a specific nuclear symmetric state. Specifically, the invention is directed to the measurement of the speed of sound in an unknown sample and comparing it to a standard.

16 Claims, 4 Drawing Sheets

GASEOUS NUCLEAR SYMMETRIC STATE AND QUANTIFICATION THEREOF

CROSS REFERENCE TO RELATED APPLICATIONS

This application claims the benefit of U.S. Provisional Application Ser. No. 60/901,362, filed on Feb. 13, 2007, which is incorporated herein by reference in its entirety.

FIELD OF INVENTION

This invention is directed to methods and apparatus of quantifying the portion of a gas in a specific nuclear symmetry state. Specifically, the invention is directed to the measurement of the speed of sound in an unknown sample and comparing it to a standard.

BACKGROUND OF THE INVENTION

MR imaging and spectroscopy require spin order in the species to be studied. This order is most commonly imposed by the application of a magnetic field, but it may also arise from spin-polarized photons (e.g. hyperpolarized gas imaging) or from rotational symmetry considerations in hydrogen. As the $H_2$ dimer approaches the moderately low temperature of tens of Kelvin in the presence of a paramagnetic relaxation site, the proton nuclei spontaneously order into the nuclear singlet state preferentially over the three triplet states. While this order cannot itself be imaged, it can be transferred to polarization of protons or heteronuclei through hydrogenation of a double bond. The resulting images of hyperpolarized $^{13}C$ and other heteronuclei show great promise for angiography, quantitative perfusion measurements and molecular imaging applications.

Up to now, the determination of the para content of the hydrogen has been based either on NMR measurements or the principle that ortho- and parahydrogen have slightly different thermal conductivities. By measurement of the thermal conductivity and comparison with a reference gas, the para content of the hydrogen can be determined. However, this measuring technique is comparatively expensive and inaccurate. Thus, because of the increasing number of uses for hydrogen and other gasses with different spin states in the near future, a simpler and more inexpensive process for determining the specific nuclear symmetric state is needed.

SUMMARY OF THE INVENTION

In one embodiment, the invention provides a method of determining the portion of a gas in a specific nuclear symmetric state comprising the steps of: streaming or placing a gas with unknown nuclear symmetry state into a first cavity; generating a sound wave in the filled cavity; measuring the speed of sound in the filled cavity; and comparing the speed of sound to a reference standard to determine the nuclear symmetry characteristics of the gas.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

Figure 1A:
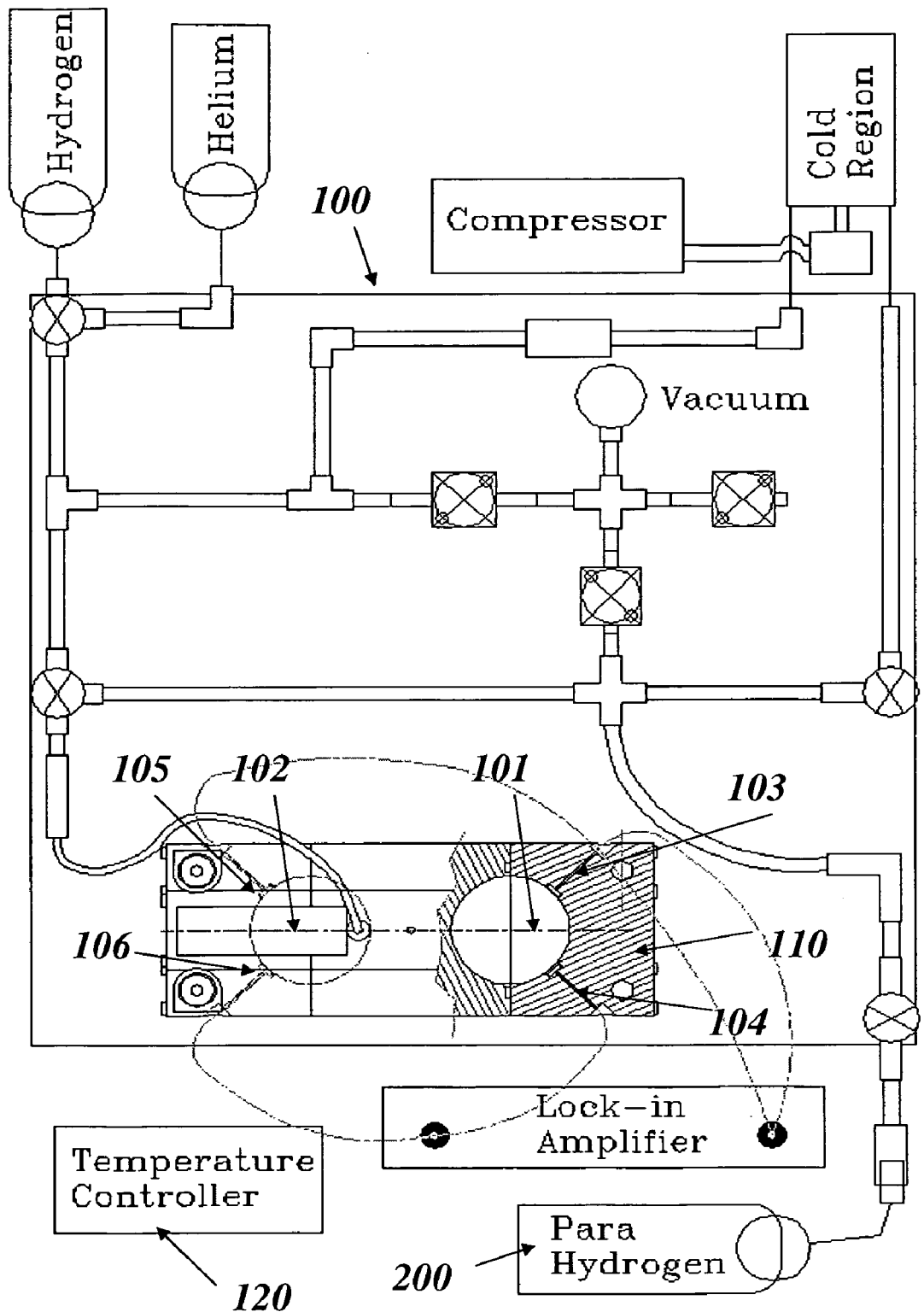
FIG. 1 shows (a) Block diagram of parahydrogen generation and measurement apparatus. (b) Detail drawing of resonant cavity measurement apparatus.

This invention relates in one embodiment to methods and in another embodiment, apparatus of quantifying the portion of a gas in a specific nuclear symmetry state. In one embodiment, using the speed of sound difference between parahydrogen and ordinary hydrogen is an accurate way to detect parahydrogen and to calculate its fraction. This method becomes more valuable when there is no NMR spectrometer available and there is a need to measure parahydrogen fraction continuously while generating.

Accordingly and in one embodiment, provided herein is a method of determining the portion of a gas in a specific nuclear symmetry state comprising the steps of: streaming or placing a gas with unknown nuclear symmetry state into a first cavity; generating a sound wave in the filled cavity; measuring the speed of sound in the filled cavity; and comparing the speed of sound to a reference standard to determine the nuclear symmetry characteristics of the gas.

Orthohydrogen and parahydrogen are two different isomers of hydrogen. In one embodiment, orthohydrogen refers to that state of hydrogen molecules in which the spins of the two nuclei are parallel (both electron spin counter-clock wise e.g.) or antiparallel with identical sign. In another embodiment, parahydrogen refers to that state of hydrogen molecules in which the spins of the two nuclei are antiparallel (one electron spin counter-clock wise and the other electron spins clock-wise e.g.) and with opposite sign. The different characteristics of orthohydrogen and parahydrogen lead to different physical properties. In one embodiment, orthohydrogen is highly combustible whereas parahydrogen is a slower burning form of hydrogen. In another embodiment, liquid parahydrogen is less prone to boil-off than ortho or thermal equillibrum hydrogen. Thus, orthohydrogen and parahydrogen can be used for different applications and their quantification quantified using the methods and apparatus described herein is essential to the efficiency of the application for which they are selected.

In another embodiment, the term "symmetry" refers to an exchange operation of one or more of the nuclear spins that leaves the nuclear spin Hamiltonian invariant. In one embodiment, the imposition of a new symmetry-operation does not need to be exact. It will be appreciated by those skilled in the art that the said Hamiltonian is the effective Hamiltonian of the nuclear spins, which governs the evolution of the nuclear magnetic moments over the relevant part of the application for which it is eventually used.

For gases, the speed of sound in the gas can be represented by the following formula:

$$v_{sound} = \sqrt{\frac{\gamma RT}{M}}$$

Where: v is the speed of sound (m/s);
γ is adiabatic constant;
R is the Gas Constant (8.314 J/molK; and
M is Molar mass in kg/mol In one embodiment, γ, the adiabatic constant is defined as the ratio between the constant volume specific heat (Cv) and the constant pressure specific heat (Cp):

$$\gamma = \frac{C_V}{C_P}$$

In one embodiment, γ for pure para-hydrogen is 0.59 while 3:1 ratio of ortho-to-para hydrogen has a γ of 0.71. In another embodiment, enthalpy, thermal conductivity, and specific heat capacity show large differences for Ortho-hydrogen and Para-hydrogen. Therefore, in one embodiment, using the speed of sound it is possible to quantify the nuclear symmetric state of the gas mixture. In one embodiment, the nuclear symmetry state sought to be determined using the speed of sound as described in the methods provided herein, is ortho state. In another embodiment, the nuclear symmetry state sought to be determined using the speed of sound as described in the methods provided herein, is a para-state.

In one embodiment, the step of measuring is done using the resonance characteristics of the first cavity or in another embodiment, the positioning of sound generating and receiving elements. Accurate measurements of the speed of sound of a gas may be made in one embodiment, using a resonator as disclosed in an article entitled Spherical Acoustic Resonators by M. Bretz, M. L. Shapiro and M. R. Moldover in volume 57 of the American Journal of Physics, incorporated herein by reference in its entirety. The resonator containing a sample of a test gas has an acoustic transmitter 103 and an acoustic receiver 104 mounted in its wall. The acoustic transmitter 103 is driven over a range of frequencies and the amplitude of the signal provided by the acoustic receiver 104 is detected for each frequency at which the acoustic transmitter is driven. The frequency at which the acoustic receiver picks up the strongest, sharpest signal ie the first resonant radial mode is detected. Since the resonating frequency is a linear function of the speed of sound of the test gas in the resonator, the speed of sound of the test gas may be determined.

For a spherical resonator of given radius, the enclosed gas will exhibit a series of acoustic resonances. The resonances are the result of three dimensional standing waves. For a perfect system the resonant frequencies (f) are a function of the root of a spherical Bessel function (z), the speed of sound (c) and the radius of the sphere (r) given by:

$$f = cz/(2\pi r)$$

In another embodiment, the radial mode is used because in this mode sound impinges on the wall of the sphere at right angles and so does not suffer energy loss due to viscous drag and so produces a sharp resonant peak which is not difficult to detect accurately.

In another embodiment, a second cavity 102 is used to provide simultaneous measurements for comparison of the gas with unknown nuclear symmetry state, with a reference standard gas in a known state of nuclear symmetry. In one embodiment, the second cavity 102 is spherical and in another embodiment, identical in size and configuration to the first cavity. In another embodiment, other sizes and configuration are used, so long as the difference between the two cavities is taken into account in quantifying the proportion of the nuclear symmetry state according to the methods described herein. In one embodiment, the means for generating and measuring sound is a piezoelectric element, or in another embodiment, any proper means for generating a detectable sound wave through the cavity, such as a microspeaker comprising a permanent magnet and the like.

In one embodiment, the difference in resonant frequencies between said first 101 and second 102 cavity used to calculate the speed of sound in the sample and reference gas respectively for quantifying the proportion of gas at an unknown nuclear symmetry state, is measured by maintaining the first 101 and second 102 cavity at a resonant frequency with a feedback circuit and digitally subtracting the counted frequencies.

In one embodiment, the reference standard gas is in the thermal equilibrium nuclear state, such as 3:1 orthohydrogen to parahydrogen respectively in another embodiment. In one embodiment, the gas having an unknown nuclear symmetry state sought to be quantified using the methods described herein and the reference standard gas with known nuclear symmetry state are chemically identical. In another embodiment, the difference in resonant frequencies between said first 101 and second 102 cavity is measured by sweeping said first 101 and second 102 cavity across their respective resonant frequencies and detecting the resonant frequency, thereby calculating the speed of sound in the sample and reference gas. In one embodiment, the first 101 and second 102 cavity are enclosed in a single block 110.

In one embodiment, the block 110 comprising the first 101 and second 102 cavities used to compare the speed of sound, is temperature controlled or in another embodiment, pressure controlled, or both in another discrete embodiment. In one embodiment, the temperature and pressure inside the first 101 and second 102 cavities are identical.

In one embodiment, the gas which nuclear symmetry is sought to be quantified is Hydrogen. In another embodiment, the gas which nuclear symmetry is sought to be quantified is Deuterium.

The following examples are presented in order to more fully illustrate the preferred embodiments of the invention. They should in no way be construed, however, as limiting the broad scope of the invention.

EXAMPLES

Materials and Methods:

Device

Figure 1:
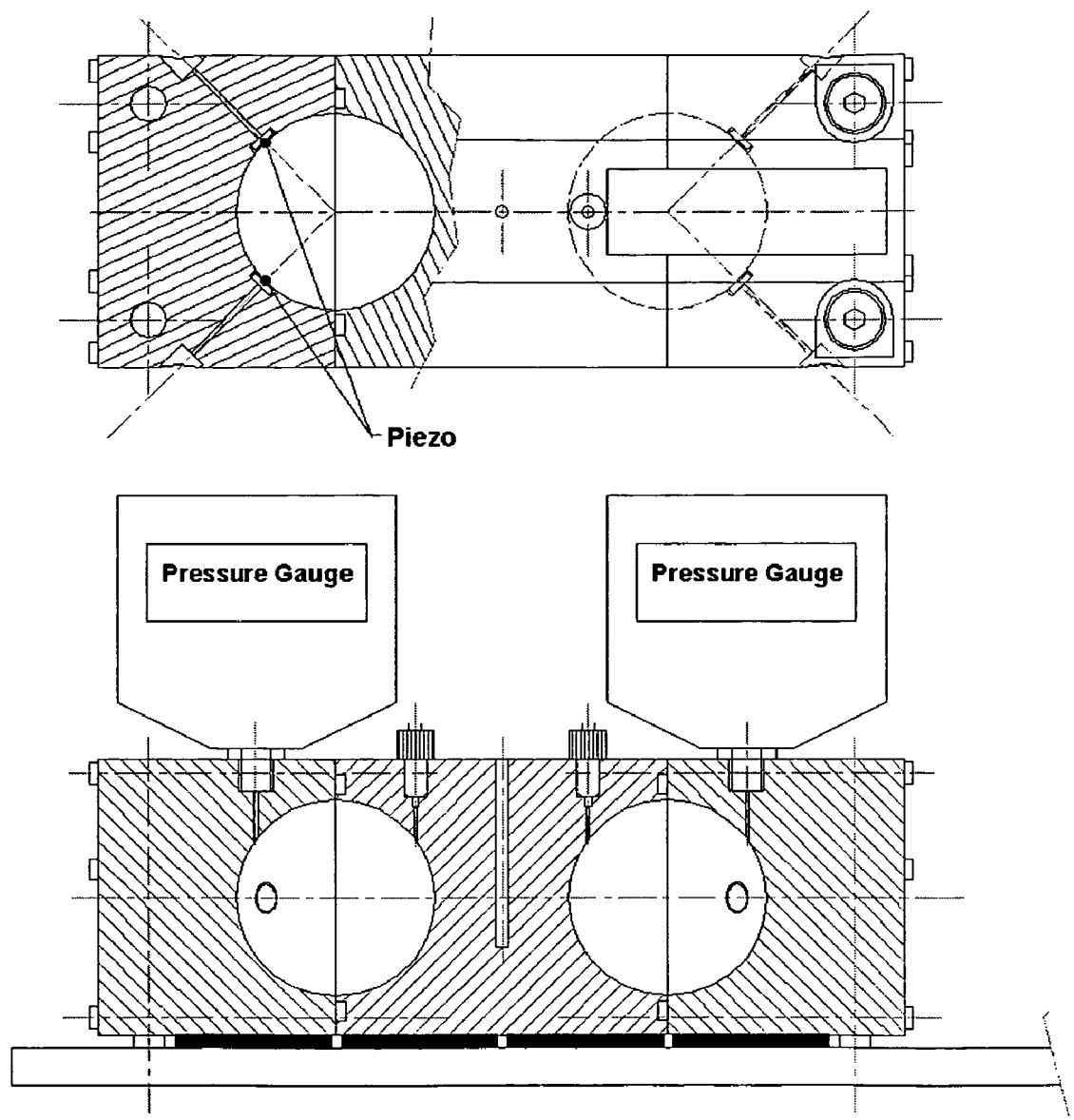

An embodiment of the apparatus 100 appears in FIG. 1. The apparatus 100 consists of two identical spherical resonant cavities of 2" diameter 101 and 102 respectively, machined from a single block of aluminum 110 and temperature-controlled via a controller 120 to approximately 20° C. The choice of a spherical cavity (101, 102) maximizes the separation between resonant modes. Each cavity 101, 102 is driven by a bare bimorph piezo element and a second element (103, 104, 105, 106) respectively), positioned at 90° may be used to detect the resonating gas. One cavity 101, is filled with the flowing parahydrogen and the other 102 with ordinary $H_2$, regulated to be at the same pressure. Note that the speed of sound depends very weakly on pressure and any value between 0.1 and 3 bars can be used while introducing negligible variation.

Example 1

Figure 2:
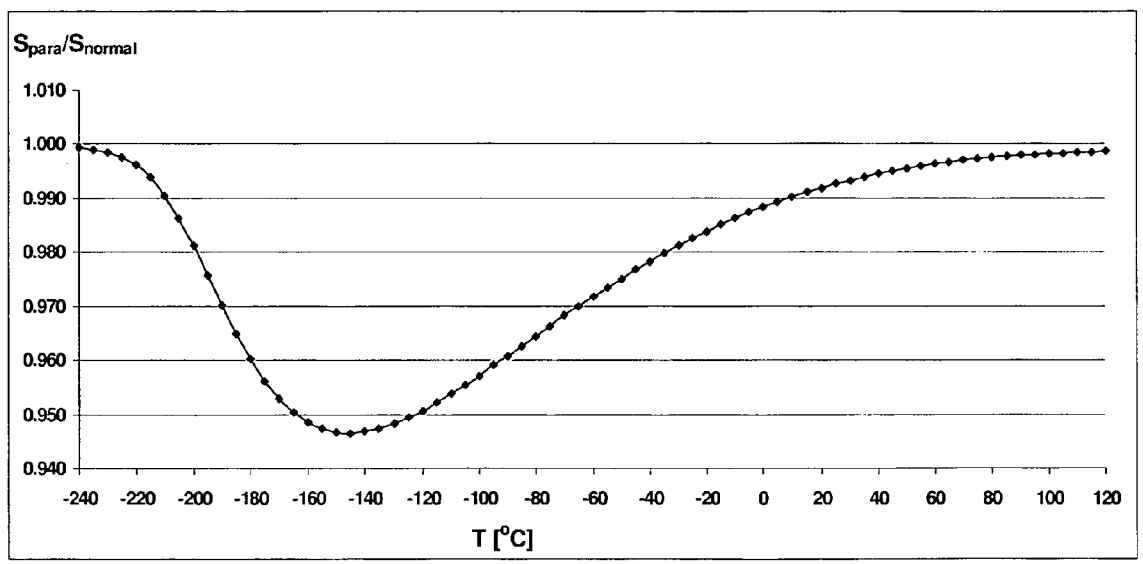
FIG. 2 shows the calculated ratio of speeds of sound in pure parahydrogen to 'normal' (unenriched) hydrogen. Note that the maximum difference of >5% occurs at −150 C, but the difference of nearly 1% at room temperature is sufficient for accurate measurement of the difference.

Difference in Measured Speed of Sound in Gasses with Different Nuclear Symmetry State Allows Quantifying of the Symmetry State Parahydrogen was created using the continuous-flow apparatus shown in FIG. 1. In order to quantify the fraction of $H_2$ in the para state during operation and to verify the quality of the reactant before use, a testing apparatus was developed based on a measurement of the speed of sound in the gas. The speed of sound differs slightly in the two forms of hydrogen because of its dependence on the heat capacity which is in turn altered by the parahydrogen's restriction to exist in only the even-numbered rotational states. FIG. 2 shows a calculated ratio of para- to normal-$H_2$ speeds. At 20° C., where this experiment is performed, the speeds of sound differ by 0.81%.

Comparison of the two cavities in apparatus 100 is advantageous because it cancels out pressure and temperature effects to a very high degree. The resonant frequency difference is measured, either by sweeping each cavity independently across its resonance, or by maintaining each cavity at resonance with a feedback circuit and digitally subtracting the counted frequencies.

Figure 3:
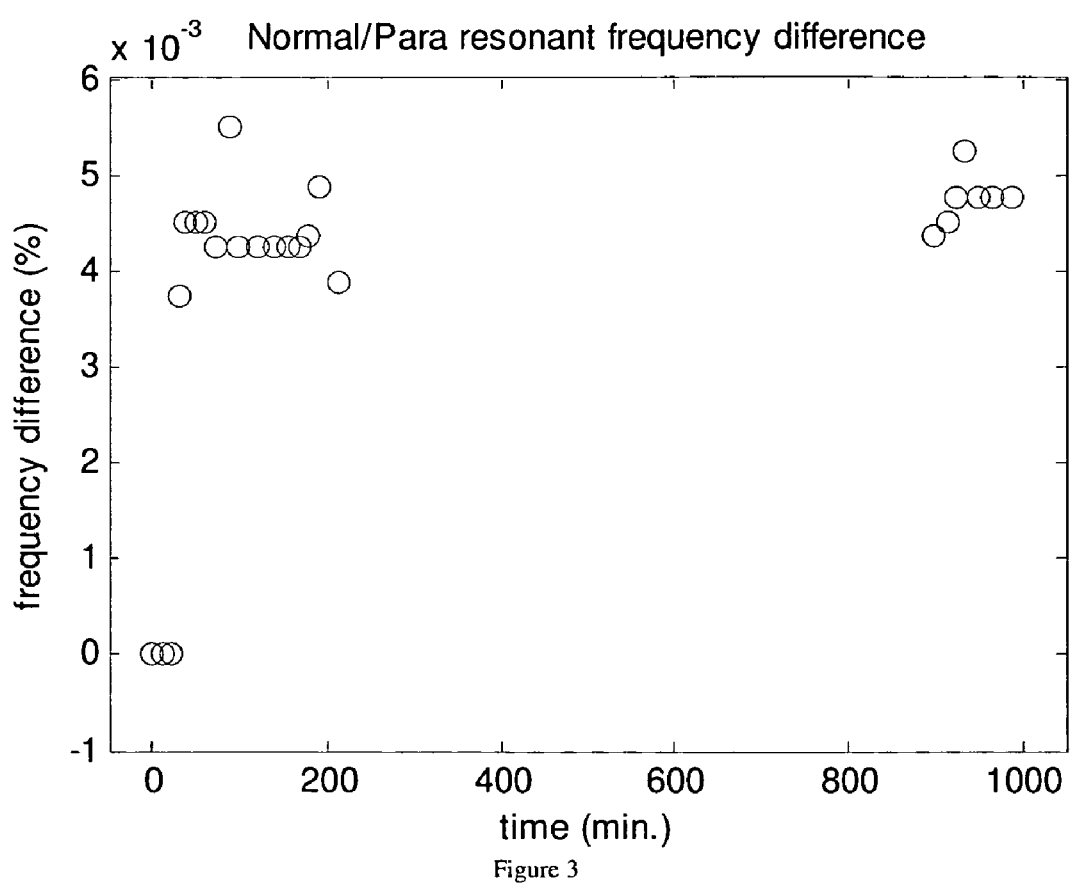
FIG. 3 shows the measured difference in the speed of sound between normal and parahydrogen as a function of time. The first three measurements are done with normal hydrogen only for comparison.

FIG. 3 shows a sample frequency difference between normal and parahydrogen created using our apparatus. The parahydrogen was stored in an aluminum cylinder 200 with internal volume 300 cc and it was refreshed periodically in an effort to measure the decay of the para state in the storage cylinder. At the beginning of the experiment, both cavities 101 and 102 were filled with ordinary hydrogen to verify that the frequencies were identical. After the experiment, a small, high-pressure sample tube was filled with first normal hydrogen and then the parahydrogen sample, both at 10 bars. Averaged NMR spectra at 4.7T showed that the normal sample signal was larger by a factor of approximately 3.6, corresponding to a para fraction of 79%+/−6% in the para sample. The average measured frequency difference in our apparatus during the measurement was 0.485%, consistent with a para fraction of 70%. The resonant frequency of each cavity was noted to be extremely stable, fluctuating by less than 0.02% during a measurement, but that the frequency occasionally shifts when the gas is evacuated and replaced. No decay in the para fraction was measured over two days of storage, indicating a lower bound on storage time in our cylinders of approximately one month.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of determining the portion of a gas in a specific nuclear symmetric state comprising the steps of: streaming or placing a gas with unknown nuclear symmetry state into a first cavity; generating a sound wave in the filled cavity; measuring the speed of sound in the filled first cavity; and comparing the speed of sound to a reference standard to determine the nuclear symmetry characteristics of the gas.

2. The method of claim 1, whereby the step of measuring is done using the resonance characteristics of the first cavity or the positioning of sound generating and receiving elements.

3. The method of claim 1, whereby the reference standard gas is in the thermal equilibrium nuclear state.

4. The method of claim 1, whereby the gas having an unknown nuclear symmetry state and the reference standard gas are chemically identical.

5. The method of claim 1, whereby the means for generating and measuring sound is a piezoelectric element.

6. The method of claim 1, whereby the flowing gas, the reference or both is Hydrogen or Deuterium.

7. The method of claim 1, whereby the specific nuclear symmetric state is para or ortho state 8. The method of claim 1, whereby a second cavity is used to provide simultaneous measurements for comparison of the gas with unknown nuclear symmetry state, with a reference standard gas in a known state of nuclear symmetry.

9. The method of claim 8, whereby the second cavity is identical to the first cavity.

10. The method of claim 8, whereby the difference in resonant frequencies between said first and second cavity is measured by maintaining the first and second cavity at a resonant frequency with a feedback circuit and digitally subtracting the counted frequencies.

11. The method of claim 8, whereby the difference in resonant frequencies between said first and second cavity is measured by sweeping said first and second cavity across their respective resonant frequencies and detecting the resonant frequency.

12. The method of claim 8, whereby the first and second cavities are spherical.

13. The method of claim 8, whereby said first and second cavity are enclosed in a single block.

14. The method of claim 13, whereby the block is temperature controlled.

15. The method of claim 13, whereby the pressure inside said first and second cavity is controlled.

16. The method of claim 13, whereby the temperature and pressure inside the first and second cavity is identical.

* * * * *